US011980421B2

(12) United States Patent
Keshishian

(10) Patent No.: US 11,980,421 B2
(45) Date of Patent: May 14, 2024

(54) SYSTEM AND DEVICE FOR PROMOTING EYE ALIGNMENT

(71) Applicant: Ara Keshishian, Glendale, CA (US)

(72) Inventor: Ara Keshishian, Glendale, CA (US)

(*) Notice: Subject to any disclaimer, the term of this patent is extended or adjusted under 35 U.S.C. 154(b) by 0 days.

(21) Appl. No.: 17/992,233

(22) Filed: Nov. 22, 2022

(65) Prior Publication Data

US 2023/0107627 A1     Apr. 6, 2023

Related U.S. Application Data

(60) Division of application No. 16/193,300, filed on Nov. 16, 2018, now Pat. No. 11,534,066, which is a continuation-in-part of application No. 15/431,207, filed on Feb. 13, 2017, now Pat. No. 10,133,091.

(60) Provisional application No. 62/294,135, filed on Feb. 11, 2016.

(51) Int. Cl.
    *G02B 27/10*      (2006.01)
    *A61B 3/00*      (2006.01)
    *A61B 3/08*      (2006.01)
    *A61B 3/14*      (2006.01)
    *G03H 1/04*      (2006.01)

(52) U.S. Cl.
CPC .............. *A61B 3/14* (2013.01); *A61B 3/0025* (2013.01); *A61B 3/08* (2013.01)

(58) Field of Classification Search
CPC ........... A61B 3/0025; A61B 3/08; A61B 3/14; A61B 3/085; G02B 5/32; G02B 27/10; G02B 27/283; G02C 7/101; G02C 7/16; G02C 7/12; G02C 2202/10; G03H 1/041
See application file for complete search history.

(56) References Cited

U.S. PATENT DOCUMENTS

| | | | |
|---|---|---|---|
| 5,094,521 A | 3/1992 | Jolson et al. | |
| 8,770,750 B2 | 7/2014 | Vendel et al. | |
| 9,254,080 B2 | 2/2016 | Oz et al. | |
| 11,534,066 B2* | 12/2022 | Keshishian | A61B 3/08 |
| 2012/0307203 A1 | 12/2012 | Vendel et al. | |
| 2014/0300859 A1 | 10/2014 | Oz et al. | |
| 2016/0081546 A1 | 3/2016 | MacDougall | |

(Continued)

FOREIGN PATENT DOCUMENTS

| | | |
|---|---|---|
| GB | 2496005 A | 5/2013 |
| WO | 2011067361 A1 | 6/2011 |
| WO | 2013035086 A1 | 3/2013 |

OTHER PUBLICATIONS

International Search Report for PCT/US2017/017667 dated May 19, 2017.

(Continued)

*Primary Examiner* — Jack Dinh
(74) *Attorney, Agent, or Firm* — Millen, White, Zelano & Branigan P.C.; William F. Nixon

(57) ABSTRACT

A system includes glasses for executing a process to correct the alignment of an eye if a misalignment condition is detected. The glasses include lens that change opacity as instructed by a processor. The system determines that an eye is not aligned correctly based on data captured by one or more sensors in the glasses. Data is captured periodically and compared to a baseline set of data. If a deviation is detected, then the appropriate lens is turned "ON" to shade the aligned eye, thereby forcing the misaligned eye to properly align itself.

13 Claims, 8 Drawing Sheets

(56) References Cited

U.S. PATENT DOCUMENTS

2016/0270653 A1    9/2016   Bailey
2016/0377864 A1   12/2016   Moran et al.

OTHER PUBLICATIONS

Office Action in corresponding EP 17714040.7 dated Jul. 3, 2020 (pp. 1-4).
EP search report dated Mar. 27, 2020 in corresponding EP19209448 {pp. 1-3) and opinion (pp. 1-4).

* cited by examiner

SYSTEM AND DEVICE FOR PROMOTING EYE ALIGNMENT

FIELD OF THE INVENTION

The present invention relates a system or device to measure and detect the direction of the eyes to promote eye alignment. More particularly, the present invention uses color sensors and reflected light and processes to detect eye direction and misalignment in order to take corrective action.

DESCRIPTION OF THE RELATED ART

If the eyes are not aligned when looking at an object, then signals sent from the eyes via the visual pathway to the cerebral cortex are not perceived properly. The brain, in turn, may ignore the signals from the affected eye if unable to reconstruct a three-dimensional image. Double vision also is noted if the eyes are not aligned. This condition causes poor development or atrophy of the pathway and may cause a loss or significant diminished depth perception or a limitation in the peripheral visual field. It is estimated that misalignment of the eyes affects about 4% of children in the United States. Adults, who have misalignment of the eyes, experience double vision.

One of these conditions may be Strabismus. Strabismus is defined as when both eyes are not aiming in the direction of the intended subject being viewed. This condition may result from a disease or disorder affecting ocular muscles, cranial nerves, or the control center of the brain that is responsible for directing eye movement. For a majority of the young pediatric population born with conditions resulting in strabismus, the treatment options initially may include corrective lenses in addition to eye patching. Some cases may require one or more surgical procedures.

An eye patch may be used to correct misalignment of the eyes. The patch over the healthy eye forces the deviated misaligned eye to direct itself to the intended field. A patch over the eye seems like a relatively benign treatment. Significant limitations, however, exist. These limitations may include physical as well as psychological or psychosocial considerations. For example, physical limitations may include a lack of compliance by the patient by removing the eye patch. Alternatively, the eye patch may become loose. Young children may be reluctant to socialize or be seen in public if required to wear eye patches for prolonged periods of time. There is also concern that prolonged patching of the non-deviated eye to correct the direction of the misaligned eye, may result in decrease in visual acuity of the non-deviated eye possible due to atrophy of the neuro-ocular pathway(s).

In some cases, if there are refractory deficiencies noted, the misalignment may be addressed by the use of corrective lenses. Corrective lenses may be needed to address refractory and optical prism axis conditions affecting one or both eyes. Corrective lenses help decrease strain on the extraocular muscles due to severe farsightedness or may be prismatic to decrease diplopia, thereby transmitting a overlapping single image to the brain.

SUMMARY OF THE INVENTION

The disclosed embodiments include fashionable, practical and cost-effective interactive eyeglasses that can be worn by a user requiring patching and accurate measurements of the deviation of the eyes. In some embodiments, the user is a child or an adult wearing the glasses to correct misalignment of the eyes. The glasses may use polarized lenses that can be scheduled or programmed to shade out the desired eye. This feature also includes the polarization of the lenses based on an algorithm that is responsive to the data collected while the subject wears the glasses. The polarized lens may act as an eye patch. A benefit of the disclosed system and device to the child and parents is the passive and non-intrusive nature of the use of the disclosed glasses. This feature, in particular, will maximize compliance by a user, or patient, of the glasses to improve long-term treatment.

One embodiment of the disclosed system and device incorporates an active scanning of a known variable of both eyes and compares images to identify the deviated eye. The data collected can be utilized for not only accurate measurement of the angle of deviation between the eyes, but also can instruct the glasses to shade out the unaffected eye, thereby forcing the deviated eye to align with the subject being viewed. These two mechanisms (the accurate measurement of angle of deviation, and the action taken to correct the misalignment) can be utilized together or separately for different diagnostic and therapeutic applications. The glasses may be programmed for an automatic "ON" and "OFF" using signal intervals. The "ON" condition causes opacity of the lens covering the non-deviated eye. The opacity of the lens forces the deviated eye to turn to the direction of the intended gaze. In another embodiment, the disclosed glasses are programmed with a separate device, such as a smart phone, using known wireless communication protocols. The wireless device is used to control the behavior of the glass, by pushing programing code lines as well as receiving data from the glasses which include variables such as the deviation direction, length, speed, xis and other.

When used as a diagnostic device in an office setting, the glasses can measure the deviation angle of the eyes with the patient wearing the glasses whereby the lenses will modify opacity with the command of the individual doing the testing and measure the data to calculate the degree of misalignment.

In some embodiments, the glasses may incorporate stand-alone corrective lenses or film. The film can be attached to the inside of a pair of glasses with corrective lenses. An additional application may apply to adults who are experiencing double vision, where the glasses can be used to occlude the non-deviated eye without impacting the daily activity that is secondary to the need for eye patching. The device controlling the glasses can be pre-programmed to occlude as prescribed by a doctor. When used for measuring the angle of deviation, the glasses will be used in the clinician's office, research or other environment with potential for traumatic head injury where the earliest sign of an impending trauma to the brain may only be subtle deviation of one or both eyes, or eyes twitching undetectable to the naked eye of the examiner. Thus, the glasses may darken the lens on a set schedule or as needed. This feature allows the user to wear an eye accessory that appears as sunglasses, as opposed to a patch. Such a device will allow a child with strabismus to receive patch therapy during school, activities, or in public without being subjected to the uncomfortable association that may take place with an eye patch.

One of the limitations of the eye patching is that the therapy is not necessarily at the time when the affected eye may be deviated. The disclosed system detects the deviation of the eye by measuring the color signature changes of the reflected light from the eye, and once deviation is noted, patches the eyes. This interactive system maximized the benefit of patching when deviation is present.

According to additional embodiments, the disclosed glasses may implement a process using a system to determine when the eyes are misaligned in order to occlude the appropriate side. Thus, the user is not subjected to constant patch therapy, or having to program the glasses to shade over an eye. Many times, the user may not be aware that his or her eyes are misaligned since the perception is depressed because of the resultant double vision caused by the non-alignment of the eyes in the same gaze direction. The disclosed embodiments detect the condition. The disclosed system also may be used to, among other things, measure the angle between the eyes individually, or one eye compared to its baseline straight gaze in all axes. This feature will allow for accurate and reproducible data collection that traditionally has been very cumbersome and non-reproducible.

When used for the correction of strabismus, the glasses are placed on the user and calibrated. A button on the frame may be pushed to initiate the calibration phase. The calibration phase may involve alternating opacity of the lenses between eyes for about 10-20 seconds each, while the individual looks straight at an object approximately 5-10 feet away. The head should be straight with the nose turned in the direction of the viewed object. The calibration process may take about 20-40 seconds for both eyes to be calibrated. An inward facing sensor collects a baseline position for the left and right eyes. The data is collected over a time frame to account for blinking or micro-positional changes. This data is stored as the baseline color fingerprint, or color signature. The eyes are monitored by left and right eye sensors. If one eye is not aligned and deviates by a specified percentage, such as 75%, of the captured signature data for a period of time, such as 15 seconds, then the opposite lens will be shaded, or turned ON, to direct the deviated eye toward alignment. All of these variables, sampling of resting position, sampling of the eyes position, the degree of variation between the resting eye position and the eye position can be adjusted as necessary for each individual case.

When the disclosed system is used to measure the deviation angle, the glasses may be worn with the calibration phase being similar to the one disclosed above. The subject then will follow specific instruction(s) to look at a certain direction while measurements are made. This data can then be used to provide an accurate degree of deviation on both horizontal and vertical axis. This feature allows for data to be collected and acted upon for promoting alignment of eyes under certain conditions. Furthermore, the system or device can implement a process to provide an eye patch environment to promote eye alignment using glasses when a need is determined. The early measurement of the small angle changes may also be used to detect early traumatic brain injury, which may manifest itself by double vision in cases such as sports injury, concussion injury of military personal, and the like. The disclosed embodiments also allow for accurate detection of the direction of the eyes individually, and any deviation of the angle between the eyes.

A method for correcting a misalignment of an eye is disclosed. The method includes capturing color signatures for a pair of eyes using a first set of sensors and a second set of sensors on glasses for the pair of eyes. The method also includes comparing the color signatures to a normal color signature for the pair of eyes. The normal signature corresponds to a normal alignment for the pair of eyes. The method also includes determining a difference for each eye between its respective color signatures and the normal signature. The method also includes determining a first eye of the pair of eyes is not aligned based on the difference. The method also includes making opaque a lens for a second eye of the pair of eyes.

A system to correct misalignment of an eye also is disclosed. The system includes glasses having a right lens and a left lens to cover a pair of eyes. The system also includes a first set of sensors corresponding to the right lens. The system also includes a second set of sensors corresponding to the left lens. The system also includes a processor coupled to the first set of sensors and the second set of sensors. The processor executes instructions stored in a memory. The instructions configure the processor to capture color signatures for the pair of eyes using the first set of sensors and the second set of sensors. The instructions also configure the processor to compare the color signatures to a normal signature for the pair of eyes. The normal color signature corresponds to a normal alignment for the pair of eyes. The instructions also configure the processor to determine a difference for each eye between the color signatures and the normal color signature. The instructions also configure the processor to determine a first eye of the pair of eyes is not aligned based on the difference. The instructions also configure the processor to make opaque the right lens or the left lens for a second eye of the pair of eyes.

A pair of glasses also is disclosed. The pair of glasses includes a frame holding a left lens and a right lens. The pair of glasses also includes a first set of sensors located proximate the left lens to capture color signatures of a left eye. The pair of glasses also includes a second set of sensors located proximate the right lens to capture color signatures of a right eye. The pair of glasses also includes a processor to compare the color signatures for the left and right eyes to a normal signature to determine whether the left eye or the right eye is not aligned and to make opaque the left lens or right lens. The darkened lens is opposite the misaligned eye.

A method for correcting a misalignment of an eye using glasses is disclosed. The method includes capturing color signatures for a pair of eyes. The color signatures include a color composition and a luminosity of light reflected by each eye. The method also includes comparing the color signatures to a normal color signature for a pair of eyes. The normal color signature corresponds to a normal alignment for the pair of eyes. The method also includes determining a difference for each eye between its respective color signatures and normal color signature. The method also includes determining a first eye of the pair of eyes is not aligned based on the difference. The method also includes making opaque a lens for a second eye of the pair of eyes.

A method for detecting a condition of an eye is disclosed. The method includes capturing color signatures for an eye. The color signatures include a color composition and a luminosity of light reflected from the eye. The method also includes generating a plurality of data sets for the color signatures. Each data set includes measured values for the color composition and luminosity. The method also includes determining a deviation within the measured values between the plurality of data sets. The method also includes making opaque a lens to align the eye.

A device to detect a condition of an eye is disclosed. The device includes a processor to receive data from a plurality of sensors to receive reflected light from an eye. The processor is configured to capture color signatures for the eye using the plurality of sensors. The color signatures include a color composition and a luminosity of the reflected light. The processor also is configured to generate a plurality of data sets for the color signatures. Each data set includes measured values for the color composition and the luminosity. The processor also is configured to determine a deviation within the measured values between the plurality of data sets. The processor also is configured to make opaque a lens to align the eye.

BRIEF DESCRIPTION OF THE DRAWINGS

Various other features and attendant advantages of the present invention will be more fully appreciated as the same becomes better understood when considered in conjunction with the accompanying drawings.

DETAILED DESCRIPTION OF THE PREFERRED EMBODIMENTS

Reference will now be made in detail to specific embodiments of the present invention. Examples of these embodiments are illustrated in the accompanying drawings. While the embodiments will be described in conjunction with the drawings, it will be understood that the following description is not intended to limit the present invention to any one embodiment. On the contrary, the following description is intended to cover alternatives, modifications, and equivalents as may be included within the spirit and scope of the appended claims. Numerous specific details are set forth in order to provide a thorough understanding of the present invention.

Figure 1A:
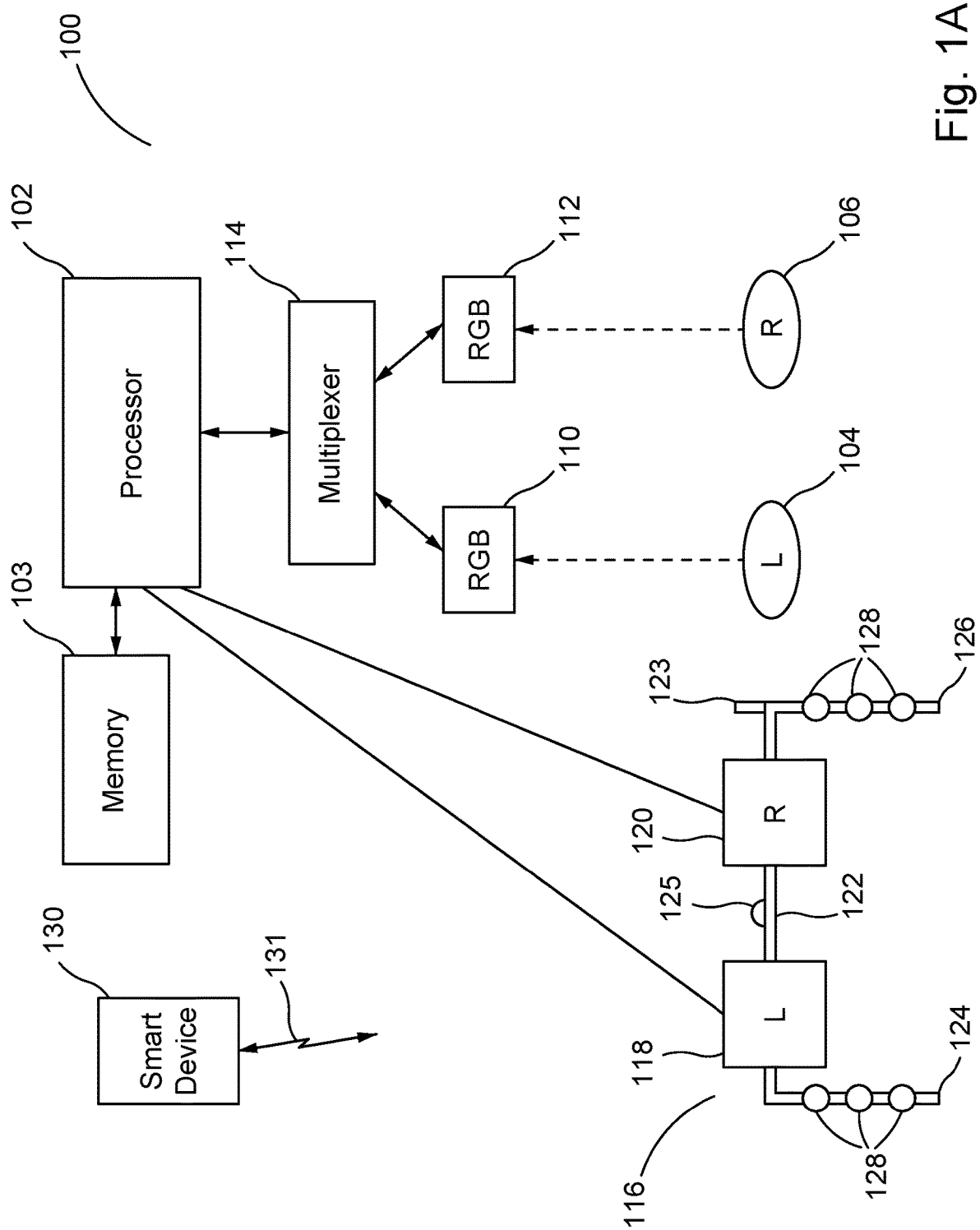
FIG. 1A illustrates a block diagram of a system for correcting eye alignment according to the disclosed embodiments.

FIG. 1A depicts a system 100 to correct eye alignment according to the disclosed embodiments. System 100 is shown using block diagrams for various components. In a preferred embodiment, system 100 may be implemented entirely on glasses 116. Alternatively, several components may reside outside glasses 116, such as on smart device 130. In the disclosed embodiments, smart device 130 may refer to any electronic device connected to other devices or networks via different wireless protocols. Smart device 130 should be able to operate to some extent interactively and autonomously as they include processors, memory, graphical user interfaces, and the ability to send and receive information over a network. Smart device 130 preferably communicates to the other components within system 100 using wireless protocols, such as Bluetooth™ or wi-fi. Examples of smart devices include mobile phones, tablets, and watches.

System 100 includes a processor 102. Processor 102 accesses memory 103. Memory 103 stores instructions that are executable on processor 102. In this configuration, processor 102 may execute the instructions to perform functions on using the other components within system 100. Processor 102 also may store results of the functions disclosed herein in memory 103.

FIG. 1A also shows left eye 104 and right eye 106. Although not shown each eye includes a pupil, an iris and sclera. The sclera may be the "white part" of the eye. Eyes 104 and 106 also have a position as the pupil and iris is moved to look at objects. A baseline position may be the position of the eye gazing forward. As eyes 104 and 106 become misaligned, more sclera may be visible than normal.

System 100 also includes red-green-blue (RGB) sensors 110 and 112. RGB sensors 110 and 112 may be sensors to receive input about eyes 104 and 106, respectively. Each side may require multiple sensors to be able to triangulate the eye positions. Preferably, the number of sensors for each side is three, or a total of six sensors. The sensors may capture color signatures or color profiles of each eye. Alternatively, the sensors may capture images of each eye. The sensors 110 and 112 may include low-resolution cameras to capture the color signatures at intervals such that the components do not continuously operate. More preferably, this interval is about 5 seconds. Alternatively, multiple signatures are captured over a time period, such as 10 seconds, with data collected from the images being averaged. The captured signatures contain data, preferably in the form of pixels, which provide color information on the targeted area of eye 104 or 106. Sensors 110 and 112 generate this information. The operation of sensors 110 and 112 in conjunction with processor 102 and multiplexer 114 is disclosed in greater detail below.

The captured image data is fed into multiplexer 114 from RGB sensors 110 and 112. Multiplexer 114 may take the received image or signature inputs for left eye 104 and right eye 106 and assign them individual addresses, such as an internet protocol (IP) address, if such features are available. An IP address refers to a numerical label assigned to each device, such as processor 102, participating in a computer network that uses the Internet Protocol for communication. An IP address may provide host or network interface identification and location addressing. The group of sensors 110 and 112 may each have their own unique addresses such that data originating from each sensor. This feature allows the data collected from each sensor to be identified by its originating location. Multiplexer 114 may use any identification protocol to note that any image or signature data is distinct. Alternatively, if sensors 110 and 112 do not have IP addresses, then multiplexer 114 may implement a process to obtain images in an ordered fashion, as disclosed in greater detail below.

The image data for eyes 104 and 106 then is provided to processor 102. Processor 102 performs operations using the image data collected by sensors 110 and 112 to determine whether eyes 104 and 106 are misaligned. This information then can be processed by either a report calculation of angular deviation or by controlling the current to the lenses 118 and 120.

System 100 also includes glasses 116. As noted above, processor 102, memory 103, sensors 110 and 112, and multiplexer 114 may reside on glasses 116. These components are embedded in the glasses as a circuit. Alternatively, some of the component functions may be executed on smart device 130. For example, sensors 110 and 112 may transmit the image data to multiplexer 114 or processor 102, which is not on glasses 116. Signals 131 may be exchanged between both devices to facilitate these operations.

Glasses 116 include left lens 118 and right lens 120. Lens 118 and 120 are polarized such that the opacity of each lens may be changed upon receipt of a signal or instruction from processor 102. Left lens 118 covers an area in front of left eye 104 and right lens 120 covers an area in front of right eye 106. Lens 118 and 120 may be any shape or size, and may have different levels of opacity.

Frame 122 holds together the different components of glasses 116. It includes a bridge between lens 118 and 120. Arm 124 extends from left lens 118 towards the left side of the head, or towards the left ear, of the user. Arm 126 extends from right lens 120 towards the right side of the head, or towards the right ear, of the user. Light emitting diodes (LEDs) 128 may be placed along arms 124 and 126. LEDs 128 light up when instructed by processor 102. LEDs 128 may emit any color, or alternate colors, as instructed.

Glasses 116 also include button 123. Button 123 is pressed to calibrate system 100 when glasses 116 are first placed on the user. Button 123 may be located any place on frame 122 and is connected to processor 102. In some embodiments, button 123 may "boot" processor 102 to reset and begin calibrating system 100.

As noted above, components of system 100 may reside on smart device 130 as functions. Transceiver 125 may communicate with smart device 130 and the components on glasses 116 by transmitting and receiving signals 131. Processor 102 may instruct components on glasses 116 in accordance with instructions received at transceiver 125. Moreover, smart device 130 may include an application having a graphical user interface (GUI) that receives input from the user and send commands to glasses 116. For example, the user may want LEDs 128 to turn ON and emit light. A signal 131 from smart device 130 instructs processor 102 to issue commands to emit the light.

Additional components may be included in system 100, but not shown in FIG. 1A. These components include nose pads, end pieces, screws to attach the components of frame 122 together, and the like. In a preferred embodiment, RGB sensors 110 and 112 are located on the bridge of frame 122 between lens 118 and 120. Multiplexer 114 also may be located on the bridge. Processor 102 and memory 103 may be located within frame 122 along arm 124 or 126.

Using system 100, various actions may be performed to promote alignment of eyes 104 and 106. These actions include polarizing lenses 118 and 120 using automatic ON and OFF signals at intervals. Smart device 130, for example, may instruct processor 102 to change the opacity of lens 118 or lens 120 for a non-deviating eye. This action forces the deviated eye to focus or align on an object as the other eye is shaded from viewing the object. For example, if right eye 106 is deviating in it alignment, then the user (or someone else) may use smart device 130 to instruct left lens 118 to become shaded to force right eye 106 to align. Alternatively, the user may cause opacity of left lens 118 using a button on glasses 116.

In another embodiment, glasses 116 may be programmed for automatic ON and OFF states. Smart device 130 may be used to program the times for ON and OFF states using an application. A signal may be sent from smart device 130, or, alternatively, processor 102 may receive instructions programming it to perform the automatic ON and OFF actions. This embodiment may implement using a wireless network and protocol, or glasses 116 may be connected to smart device 130 (or any computer) to program the specified times to change the opacity of lenses 118 and 120. The programming embodiments may be useful when known times of eye alignment deviation are known. Late afternoon or evening times could be indicated as times when the user is tired, or if system 100 determines that glasses 116 have been worn for an extended period of time.

Figure 1B:
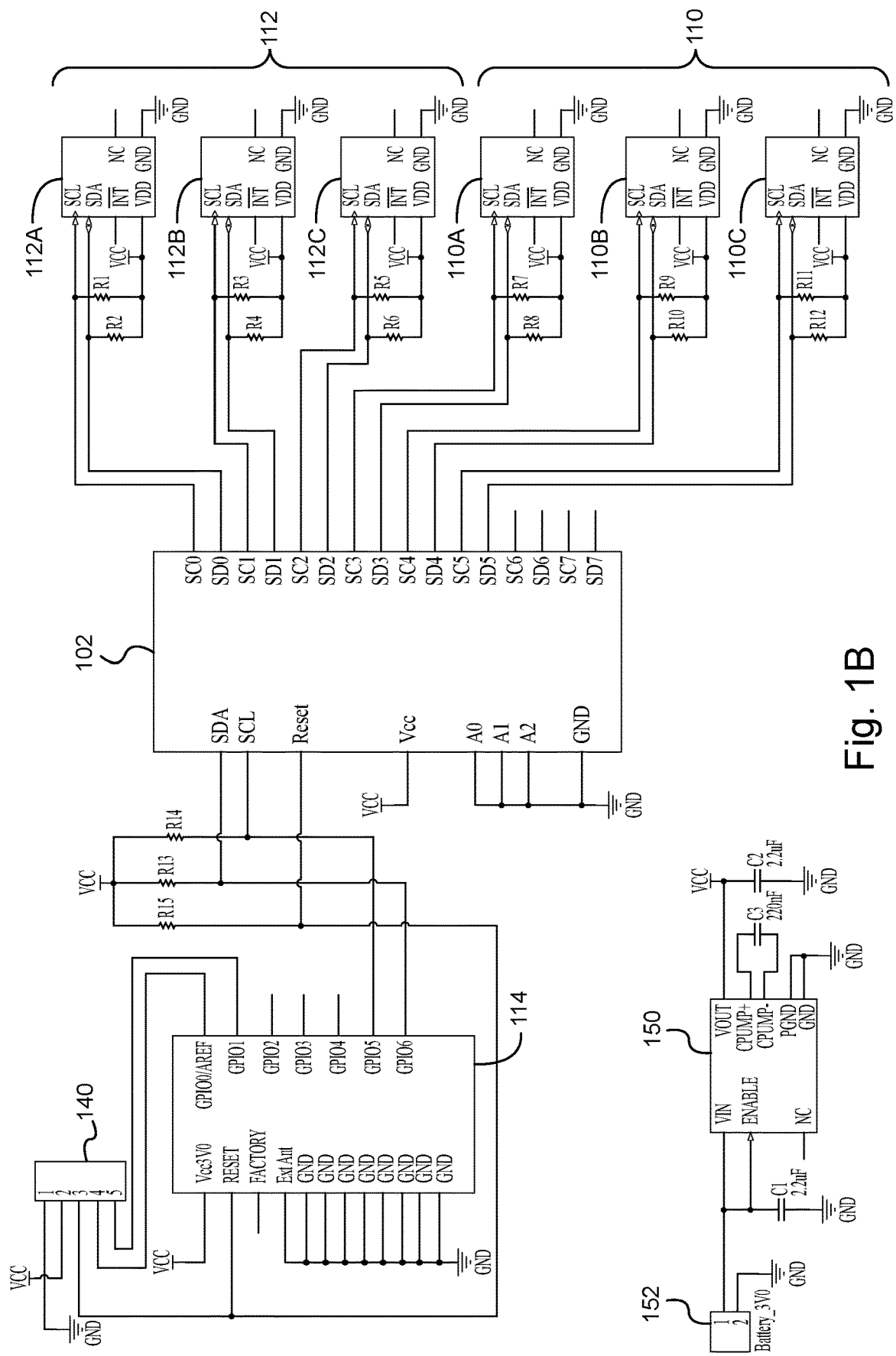
FIG. 1B illustrates a schematic diagram of components for use within the system according to the disclosed embodiments.

FIG. 1B depicts a schematic diagram of components for use within system 100 according to the disclosed embodiments. FIG. 1B may be a circuit diagram showing the configuration between sensors 110 and 112, processor 102, and multiplexer 114. FIG. 1B also shows a voltage regulator circuit 150 for use within system 100.

As shown, processor 102 is coupled to multiplexer 114 and sensors 110 and 112. Sensors 110 include a set of sensors 110A, 110B, and 110C. Sensors 112 include a set of sensors 112A, 112B, and 112C. As disclosed above, three sensors may take images of each eye. Additional sensors also may be used. Each sensor may receive a signal from processor 102 and returns a signal in response.

In some embodiments, sensors 110 and 112 do not have unique IP addresses. Thus, processor 102 may not be able to determine which image comes from which sensor. For example, the disclosed embodiments do not want to confuse image data from sensor 110B with that from sensor 110C. In this instance, information between processor 102 and sensors 110 and 112 are routed through multiplexer 114 for proper labeling.

Multiplexer 114 may assign an individual port to read only one sensor during a cycle. In some embodiments, a cycle may a millisecond or less. Thus, multiplexer 114 will instruct processor 102 which sensor to signal to capture the image data. Multiplexer 114 assigns a unique IP address to the indicated sensor. As the sensor captures image data for that cycle, the image data can be tagged with the assigned IP address from multiplexer 114 so as to separate it from image data from other sensors. Multiplexer 114 then moves to the next sensor to repeat the steps to obtain data from that sensor.

For example, multiplexer 114 instructs processor 102 to obtain data from sensor 112A. Multiplexer 114 assigns a unique IP address for sensor 112A during this process. Sensor 112A captures image data of right eye 106. The captured image is tagged with the IP address and sent to processor 102. Multiplexer 114 instructs processor 102 to move to sensor 112B and assigns a unique IP address to that sensor. Sensor 112B captures image data of right eye 106 and sends it to processor 102. These steps are repeated until image data is provided by every sensor. Multiplexer 114 assigns new IP addresses when the next batch of image data are captured.

Multiplexer 114 also may receive the image data and provide it to connector 140. Connector 140 includes ports that may connect to memory or data storage, such as memory 103. Connector 140 also may connect to a transceiver to receive and transmit information, such as transceiver 125.

System 100 also may include voltage regulator 150, which provides a constant voltage to processor 102, sensors 110 and 112, and multiplexer 114. Voltage VCC is provided within the circuit shown in FIG. 1B. Voltage VCC may be a direct current (DC) voltage of about 3.0 volts. Voltage regulator 150 may be coupled to a battery 152 that provides power to the regulator. It removes any noise or oscillation from the power provided by battery 152. Battery 152 may recharge through port 2 of connector 140.

The circuit of FIG. 1B includes other components connected to processor 102, sensors 110 and 112, multiplexer 114, connector 140, and voltage regulator 150 that are not discussed in great detail. These components include resistors R1 and R2 coupled to sensor 112A, each having a resistance of about 10 kohms. Resistors R3 and R4 are coupled to sensor 112B and resistors R5 and R6 coupled to sensor 112C, also having resistances of about 10 kohms. Resistors R7 and R8 are coupled to sensor 110A. Resistors R9 and R10 are coupled to sensor 110B. Resistors R11 and R12 are coupled to sensor 110C. Resistors R7-R12 also has resistances of about 10 kohms. Resistors R13, R14, and R15 also have resistances of about 10 kohms and are coupled to between processor 102 and multiplexer 114. Voltage regulator 150 includes capacitors C1 and C2 having a capacitance of 2.2 uFarads. Capacitor C3 is coupled to voltage regulator 150 and has a capacitance of 220 nFarads. These values for the resistors and capacitors are provided for illustrative purposes only. The disclosed resistors and capacitors may have other values other than those described above.

Figure 1C:
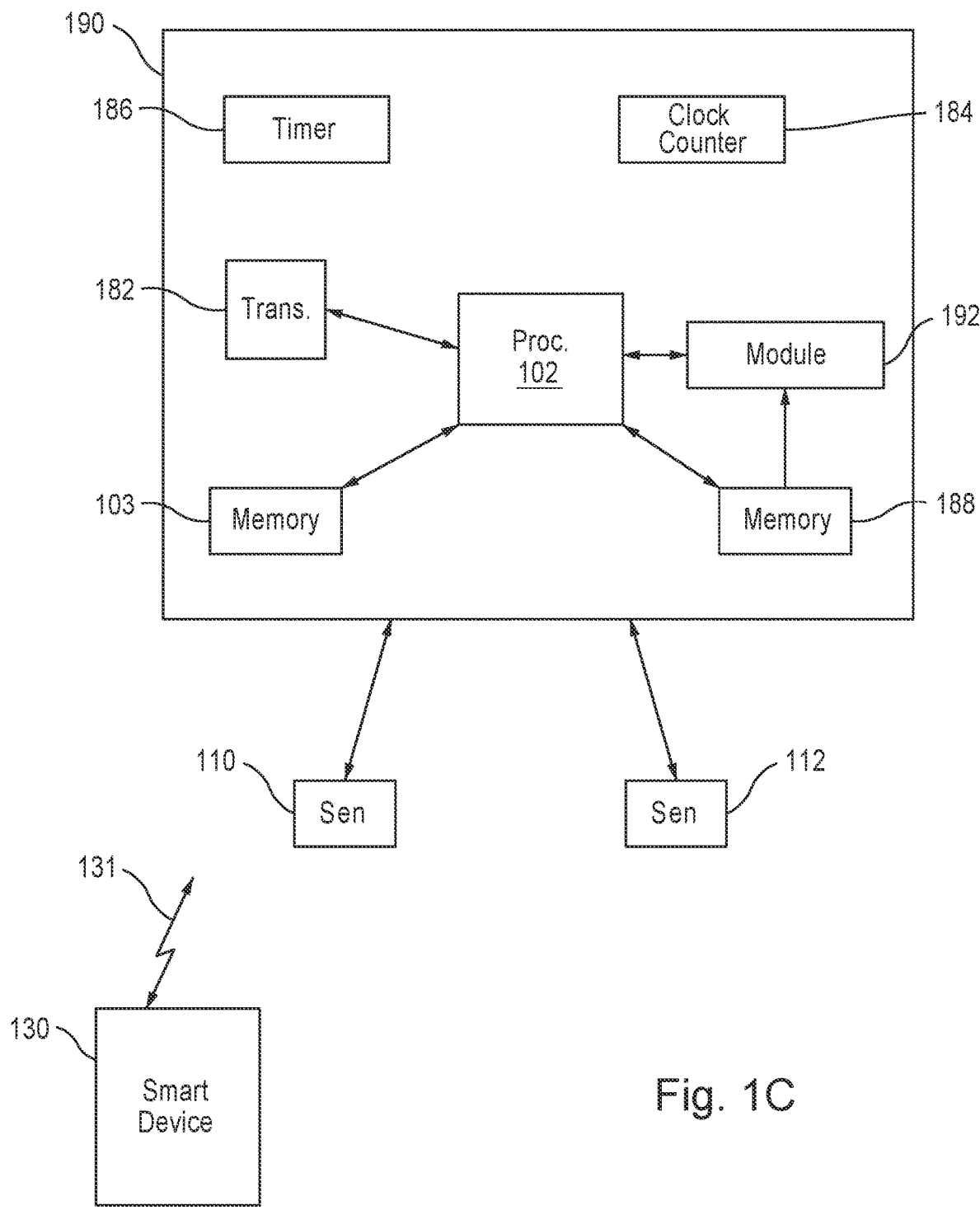
FIG. 1C illustrates a block diagram of the system for correcting eye alignment using a semiconductor chip according to the disclosed embodiments.

FIG. 1C depicts a block diagram of system 100 for correcting eye alignment using a semiconductor chip 190 according to the disclosed embodiments. The embodiments disclosed by FIG. 1C may implement the same components as shown in FIG. 1A, except that semiconductor chip 190 is used to perform the functions disclosed herein. In some embodiments, chip 190 includes processor 102, memory 103, and multiplexer 114. In other embodiments, processor 102 may perform the functions of multiplexer 114, shown as multiplexer module 192. Processor 102 may do this by executing an algorithm that performs the multiplexer function embodied in module 192. This embodiment may speed up the detection process, which allows additional functionality with glasses 116 and system 100.

Semiconductor chip 190 also includes transceiver 182, which allows signals to be received and transmitted by semiconductor chip 190. Transceiver 182 preferably uses radio-wave technology to communicate over short distances, such as 10 meters or less. Transceiver 182 may be a Bluetooth™ device that sends and receives radio waves over a band of different frequency channels. Thus, chip 190 may connect to sensors 110 and 112 using Bluetooth™ standard for connecting devices. Chip 190 also may connect to smart device 130 using transceiver 182.

Other components of chip 190 include one or more timers 186. Timer 186 may countdown periods between actions such that information does not overwhelm processor 102 or system 100. Data from sensors 110 and 112 may be captured at a higher rate than may be processed using chip 190. Thus, the data may need to be buffered in memory 103 before it can be processed. Using the buffered data, processor 102 may perform additional actions, such as measuring the speed of deviation or potential twitches of eyes 104 and 106. Chip 190 also includes one or more clock counters 184 that may work in tandem with timer 186 to indicate when data is to be accessed, stored, and the like. Clock counter 184 also may provide clock stamp information for data as it comes into chip 190.

Memory 188 is shown. Memory 188 may be accessible by processor 102 to execute instructions for algorithms to be used in processing data from sensors 110 and 112. Memory 188 also may be accessible by processor 102 to invoke module 192 based on the algorithms to process the incoming data. It should be noted that sensors 110 and 112 may obtain any information about eyes 104 and 106 to determine deviation of the eyes or other information disclosed herein. Chip 190 receives data streams from sensors 110 and 112 as it can handle the incoming data in a faster manner due to increased processing power. The data streams are processed using firmware between processor 102, memory 103, and other components.

Figure 2:
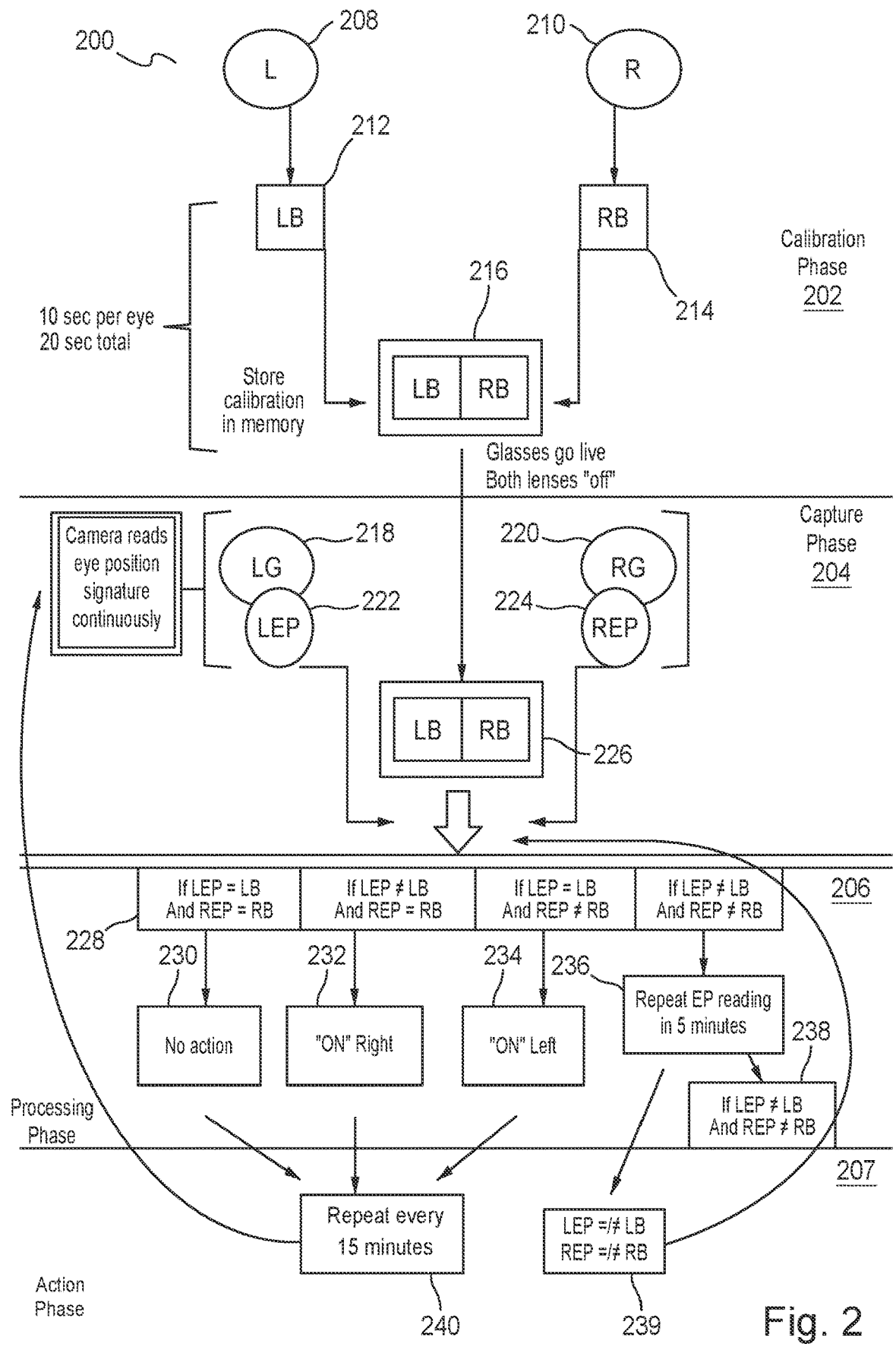
FIG. 2 illustrates a flow diagram of a process to correct eye alignment according to the disclosed embodiments.

FIG. 2 depicts a flow diagram 200 of a process to correct eye alignment according to the disclosed embodiments. The process shown in FIG. 2 may be implemented by system 100, including glasses 116. Flow diagram 200 provides an overview of the disclosed processes that are disclosed in greater detail below.

Within FIG. 2, the following abbreviations may refer to the following terms:
L Left eye
R Right eye
LB Left baseline position for the left eye
RB Right baseline position for the right eye
LG Left eye gaze
RG Right eye gaze
LEP Left eye position
REP Right eye position
"ON" Opaque state for a lens (energized)
"OFF" Translucent state for a lens (not energized)

The process disclosed by flow diagram 200 includes three phases: a calibration phase 202, a capture phase 204, a processing phase 206 and an action phase 207. Each phase includes steps performed by system 100. Other steps may be performed within the phases without deviating from the scope of the invention. The steps are broken into phases to better show the different operations performed by system 100.

When glasses 116 are first placed on the user, they need to be calibrated. Calibration phase 202 accomplishes this action. To initiate calibration phase 202, the user presses button 123 on the side of frame 122. Calibration phase 202 alternates opacity of lenses 118 and 120 to calibrate the data as a baseline for further operations.

Steps 208 and 210 execute by detecting left eye 104 and right eye 106. The user places glasses 116 on his or her nose and ears, and presses button 123. Processor 102 instructs RGB sensors 110 and 112 to detect each eye. Step 212 executes by capturing an image by RGB sensor 110 while left eye 104 stares straight ahead. Step 214 executes by capturing an image by RGB sensor 112 while right eye 106 stares straight ahead. Preferably, the user stares at an object approximately 3-6 feet away, with his or her head turned in the direction of the object. Step 212 and 214 may alternate such that each one is performed for about 10 seconds each for a total period of 20 seconds for both eyes to be calibrated.

Using the collected images, processor 102 may determine the baseline positions for each eye when looking straight ahead. The data for the baseline positions is stored in memory 103 in step 216. The data may represent a portion of the eye, captured by the image, which is "white" or not part of the pupil and iris. After storing the data, step 216 also has glasses 116 go "live." Both lenses 118 and 120 are turned "OFF" such that they are not shaded.

System 100 moves to capture phase 204. Capture phase 204 refers to the steps executed to capture the images for use in the disclosed process. Step 218 executes by a camera, such as RGB sensor 110, capturing an image of the left gaze of left eye 104. Step 220 executes by capturing an image of the right gaze of right eye 106 by, for example, RGB sensor 112. The capture of the images may occur when instructed by processor 102. Step 222 executes by determining a left eye position for left eye 104 while capturing its image. Step 224 executes by determining a right eye position for right eye 106 while capturing its image. These positions are forwarded to processing phase 206.

Step 226 executes by receiving or retrieving the left baseline and right baseline data for each eye in calibration phase 202. Thus, when entering processing phase 206, the disclosed process receives image data for baselines on each eye and image data for left eye position and right eye position for each eye. Position may be shown by the amount of sclera in the image, or white part of the eye. The dark portions of the image may be the pupil and the iris. The pupil and the iris determine the eye position. For a misaligned eye, the pupil and iris will not match the baseline positions of these components of the eye.

Multiplexer 114 may take the captured images and assign each one an individual address for identification by processor 102. The captured images also may be stored in memory 103 with the assigned addresses. The addresses allow processor 102 to differentiate between images from different eyes, so it will not compare an image for left eye position to an image for right eye baseline.

Process phase 206, therefore, receives the eye image data from calibration phase 202 and capture phase 204. Step 228 executes by performing an analysis on the received image data. The result of the analysis then determines what action, if any, should be taken with regard to glasses 116.

Step 228 determines the relationship of the left eye baseline data with the left eye position data and the relationship of the right eye baseline data with the right eye position data. These relationships determine whether action will be taken in shading either left lens 118 or right lens 120. Thus, if left eye position data is approximate to the left baseline data and the right eye position data is approximate to the right baseline data, then step 230 executes by taking no action.

In other words, using the situation above, the captured images show that the position of the eyes reasonably matches the baseline images. The match need not be exact. The disclosed embodiments may set a percentage needed to be acceptable. For example, the eyes are considered aligned properly if the position data of the eyes determined in capture phase 204 matches 75% of the baseline position data. No measures need to be taken by glasses 116. System 100 may compare the images to determine the percentage of matches of the pixel values between the images. The addresses assigned by multiplexer 114 helps with matching the proper image data with the proper baseline data, and that the appropriate left and right pairs of data are used. In other words, the left eye position image is not used in conjunction with a right eye position image from the previous hour.

If step 228 determines that the left eye position image does not approximately match the left baseline image while the right eye position image does approximately match the right baseline image, then step 232 executes by sending an instruction to turn right lens 120 "ON." This condition indicates that left eye 104 is misaligned. The position in the image captured in step 218 does not adequately match the baseline position. By turning right lens 120 "ON," system 100 forces left eye 104 to aligned itself. Right eye 106 is aligned properly and does not need to be corrected. The threshold of what may be considered a match or not can be adjusted as necessary to accommodate for variation in lighting, environment and the like.

If step 228 determines that the left eye position image does approximately match the left baseline image while the right eye position image does not approximately match the right baseline image, then step 234 executes by sending an instruction to turn left lens 118 "ON." In other words, step 234 performs the opposite action of step 232. Right eye 106 is misaligned and left lens 118 is shaded to correct the alignment.

If neither position image approximately matches the appropriate baseline position image, then an error condition may have occurred. Such a condition may indicate that a correction needs to take place to capture the appropriate image data for another comparison. Thus, step 236 executes by repeating the eye position reading, or capture, in specified time period, such as 5 minutes. This time period allows the eyes to align themselves. Misalignment in both eyes may occur for extreme circumstances and should not last for an extended period of time. Step 238 executes by determining whether both eye position images still do not approximate the baseline position images. If yes, then flow diagram 200 returns to calibration phase 202. If no, then step 239 executes by having flow diagram 200 take the new captured images and re-execute step 228.

Action phase 207 occurs after processing phase 207 where subsequent steps are taken to repeat the disclosed process. Thus, step 240 executes by repeating flow diagram periodically. Preferably, step 240 returns to capture phase 204. In a preferred embodiment, this period may be every 15 minutes. Alternatively, this period may be any time length suitable to determine eye alignment. In some embodiments, the user may program processor 102 to perform capture phase 204 using smart device 130. Thus, system 100 will capture images and compare them to the baseline images using processor 102 to determine what course of action to take to align the appropriate eye, if needed.

Figure 3A:
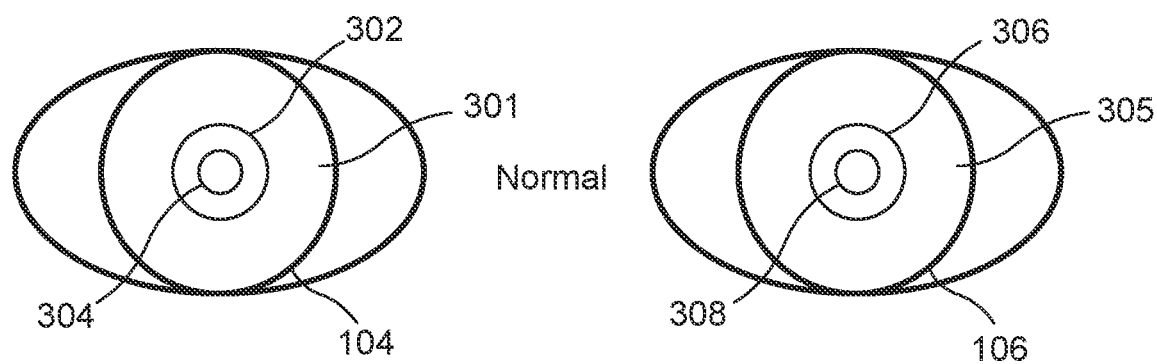
FIG. 3A illustrates the eyes in a normal position according to the disclosed embodiments.
Figure 3B:
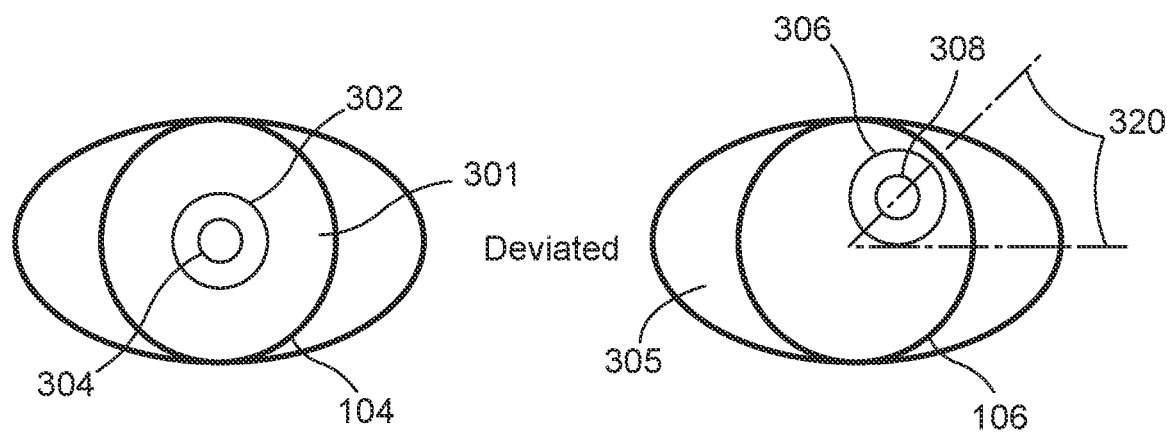
FIG. 3B illustrates an eye in a deviated position in relation to the other eye according to the disclosed embodiments.

FIG. 3A depicts eyes 104 and 106 in a normal position according to the disclosed embodiments. FIG. 3B depicts eye 106 in a deviated position in relation to eye 104 according to the disclosed embodiments. FIGS. 3A and 3B are provided for illustrative purposes to show the difference between eye 106 from the normal to deviated position. In other embodiments, eye 104 may deviate from its normal position or both eyes may be deviated.

Eye 104 includes pupil 302 with iris 304. Eye 104 also includes sclera 301. Eye 106 includes sclera 305, pupil 306, and iris 308. In FIG. 3A, the position of pupils 302 and 306 within their respective eyes is substantially similar. A captured color signature of eyes 104 and 106 in the normal position would show pupils 302 and 306 approximately in the center of the eyeballs. A distance from a midline between eyes 104 and 106 for each pupil would be approximately the same. In other words, if one measured a distance from the midline to pupil 302 would be about the same as the distance from the midline to pupil 306. Further, a distance between the pupils 302 and 306 to the outer radiuses of eyes 104 and 106 should be substantially the same.

Referring to FIG. 3B, eye 106 is deviated from the normal position. Pupil 306 has moved to the upper left of eye 106. As shown, pupil 306 is not aligned with pupil 302, either in the horizontal or vertical plane. Pupil 306 has an angle of deviation 320 that is the angle between the center of pupil 306, or iris 308, and the center of eye 106. Angle of deviation 320 may be calculated using a process. In some embodiments, smart device 130 may implement a process to determine the angle of deviation for a pupil within a possibly deviated eye.

As can be seen, when eye 106 of FIG. 3B is compared to eye 106 of FIG. 3A, differences exist. When eye 106 is compared to eye 104, differences also are detectable. The disclosed embodiments may compare a potentially deviated eye to a normal position using system 100. System 100 may capture the color signature of eyes 104 and 106 using sensors 110 and 112. These signatures are compared against the signatures for the normal position of the eyes to determine whether misalignment is occurring.

Figure 4:
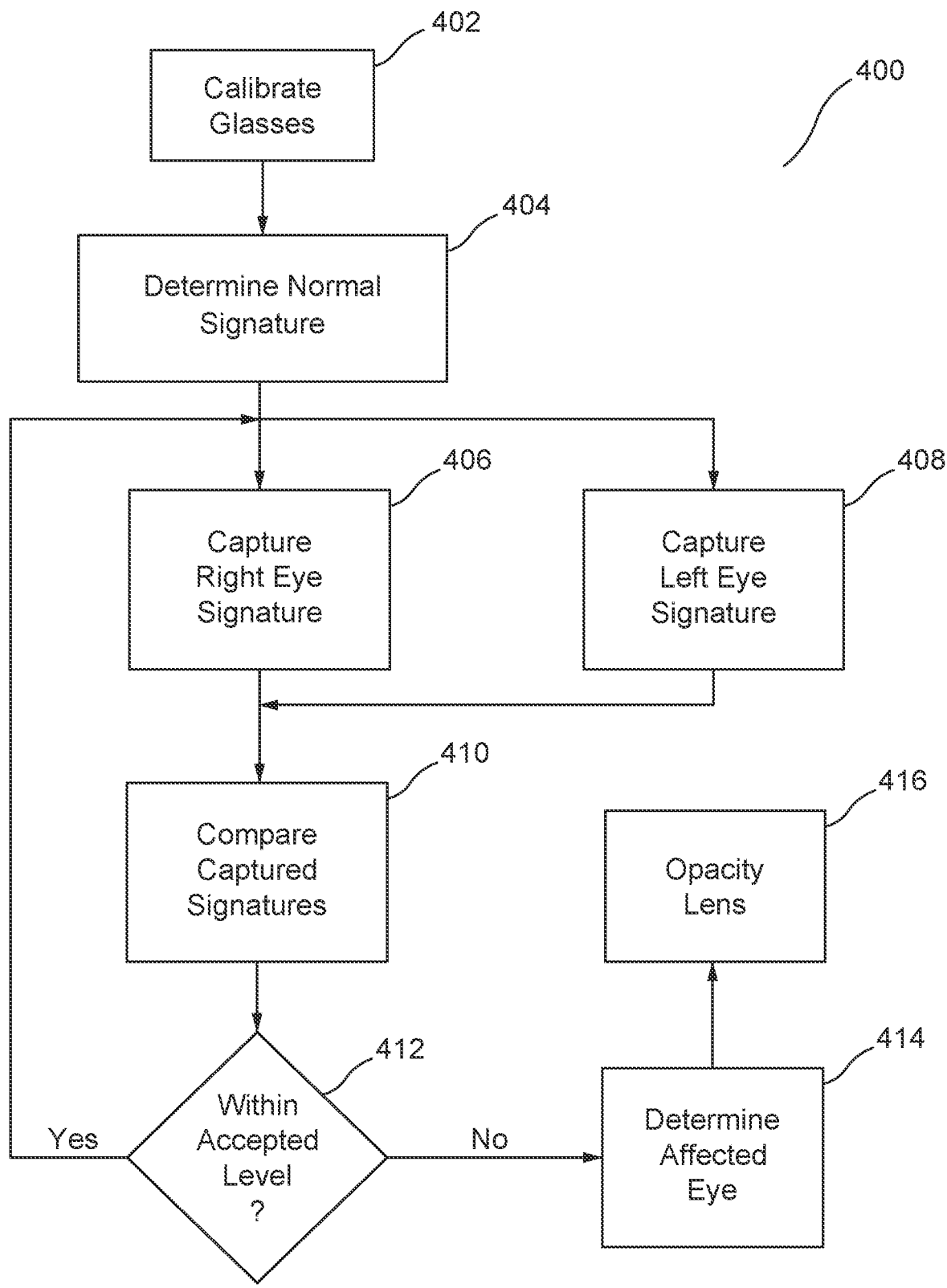
FIG. 4 illustrates a flowchart for aligning a deviated eye according to the disclosed embodiments.

FIG. 4 depicts a flowchart 400 for aligning a deviated eye 106 according to the disclosed embodiments. Flowchart 400 complements flow diagram 200. Flowchart 400 may disclose the steps that are executed using processor 102 in order to determine whether an eye is deviated and to take corrective action using glasses 116.

Step 402 executes by calibrating the glasses. This step also captures the color signatures for the eyes on the normal position. As disclosed above, a calibration phase may alternate opacity of lenses 118 and 120 for about 10 seconds each while the user looks straight ahead. System 100 collects a baseline position for the eyes. As disclosed with reference to FIG. 1B, each sensor 110 or 112 may be instructed to capture the color signature individually using multiplexer 114. Many signatures may be captured and sent to processor 102. Step 404 executes by determining a normal signature spectrum for eyes 104 and 106 based on the baseline position(s). The determination may occur by averaging the data values of the signatures captured in step 402. In some embodiments, the color profile for the normal signature spectrum matches the eyes in FIG. 3A, wherein the sclera 301 and 305 are substantially white while pupils 302 and 306 are not.

Step 406 executes by capturing a right eye color signature. Step 408 executes by capturing a left color signature. These steps may be executed simultaneously. System 100 may execute the steps alternately. As disclosed above, sensors 110 includes three sensors that capture the color signature of eye 104. The sensors capture the data when instructed using multiplexer 114 so that processor 102 can determine from which sensor captured the signatures. The capture signatures from the three sensors 110 may be combined to generate the color signature for eye 104. Step 408 performs these same actions for eye 106 using sensors 112.

Steps 404, 406, and 408 may be executed using multiplexer 114 to assign unique IP addresses, as disclosed above. The information between processor 102 and sensors 110 and 112 are routed through multiplexer 114 for proper labeling when the sensors do not have IP addresses. Multiplexer 114 assigns unique IP addresses when instructing processor 102 to capture the color signature using each sensor. The feature allows system 100 to identify which sensor capture a color signature as it is used for further processing. Thus, for example, the disclosed embodiments avoid using color signature from sensor 110B for determinations about the condition of right eye 106.

Step 410 executes by comparing the captured color signatures for each eye to the normal color signatures generated in step 404. Specifically, differences between the color values in the signatures are determined. In some embodiments, the signatures include pixel values having a specified location therein. A difference between these values indicates a deviation from the normal position of the eye. In other embodiments, the capture color signatures may be compared against each eye. These steps may be repeated over a period of time such that many color signatures are captured and used in further operations.

Step 412 executes by determining whether the differences between the captured signatures and the normal signature are significant enough to indicate one of the eyes is not aligned. For example, if an eye is not aligned within 75% for signatures captured over a period of 15 seconds, then a deviation condition is occurring. Referring back to FIG. 3B, eye 106 would have sclera 305, and its corresponding color, in the location where pupil 306 should be. The same condition exists with the location of pupil 306 in FIG. 3B. When compared to eye 106 in FIG. 3A, more than a 25% difference is determined between the captured signatures and the normal signature. The percentage for an acceptably difference may not be limited to 75%. In other embodiments, a percentage may not be used. Instead, the disclosed embodiments may determine whether differences exist at specific locations in the signatures, such as the position of the pupils.

If step 412 is yes, then the eyes are aligned. Flowchart 400 returns to steps 406 and 408. System 100 may wait for a period of time before capturing color signatures for the eyes. If step 412 is no, then step 414 executes by determining which eye is deviated or not aligned. Processor 102 may identify the sensors proving the capture signature determined in steps 410 and 412 by using the information provided by multiplexer 114. Step 416 executes by opacifying the corresponding lens to correct the misaligned eye. Using the above example, system 100 determines that eye 106 is not aligned or is deviated from the normal eye position. Glasses 116 makes lens 118 opaque to force eye 106 to correct its alignment.

Using the process disclosed above, system 100 may improve alignment of the eyes without the need for special glasses or eyepatches beyond what may be needed for optical correction. Further, system 100 may detect a deviation as it occurs, thereby forcing an eye to correct itself in a timely manner. This process may be executed automatically and without intervention by the user or a third party. Further, data may be stored on the captured color signatures of the eyes for additional analysis.

In some embodiments, smart device 130 may execute processes to determine eye alignment. These processes may determine an angle of deviation for pupil of an eye. Smart device 130, using an application, may capture the images of the eyes over a period of time and determine any change in the angle of deviation for the pupil of an eye. This information may be used for additional treatment. It also may be used with system 100 to better identify when an eye is not aligned.

Figure 5:
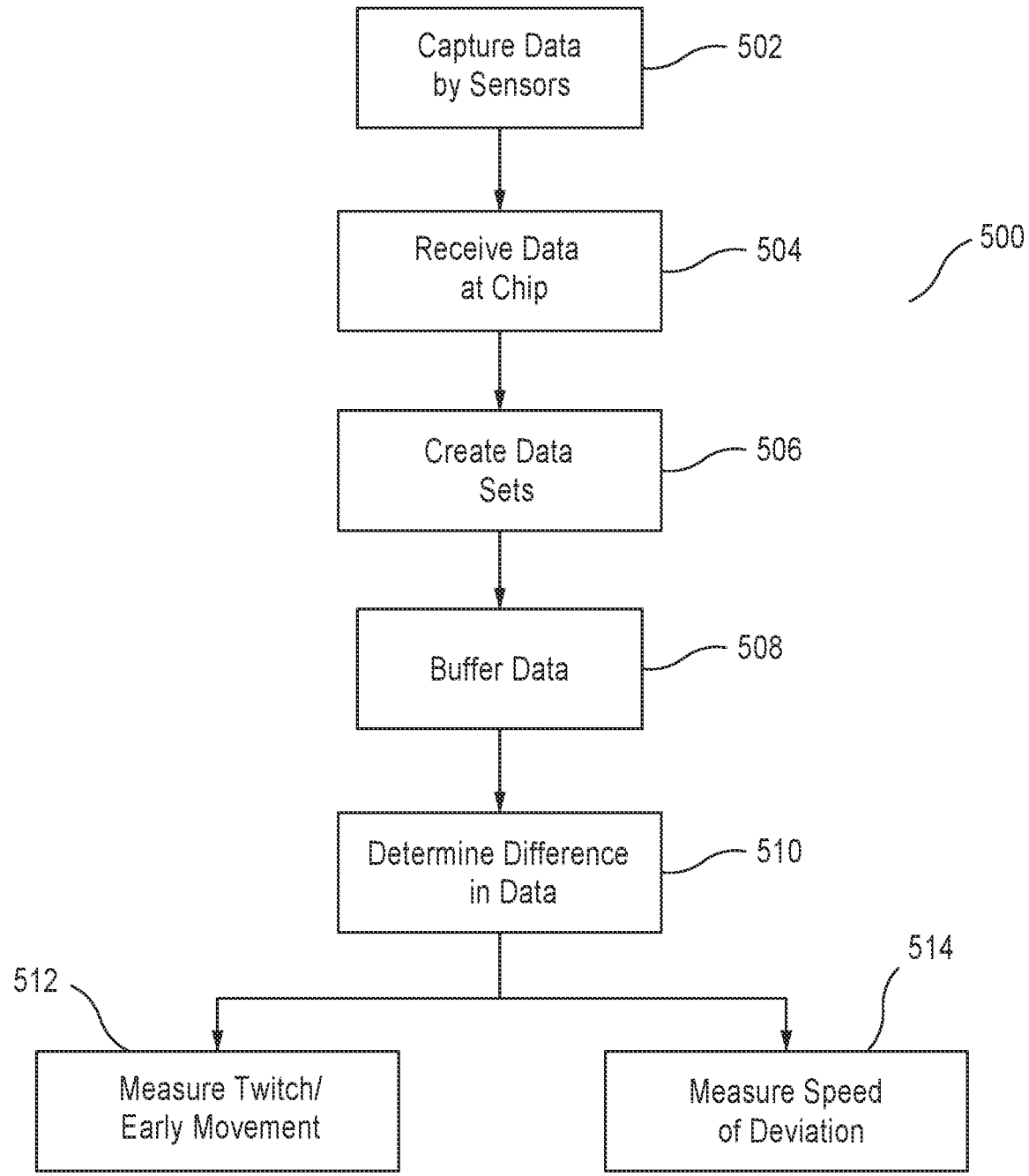
FIG. 5 illustrates a flowchart for determining a twitch, early movement, or a speed of deviation for the eyes according to the disclosed embodiments.

FIG. 5 illustrates a flowchart 500 for determining a twitch, early movement, or speed of deviation for one of eyes 104 and 106 according to the disclosed embodiments. Flowchart 500 may use the embodiment of system 100 shown in FIG. 1C with semiconductor chip 190. Chip 190 allows the incoming data streams from the sensors to be processed faster such that additional functionality is provided by system 100 and glasses 116.

Step 502 executes by capturing data for eyes 104 and 106 using sensors 110 and 112, as disclosed above. For flowchart 500, any type of data for the eyes may be captured. The captured data are formed into data streams. The data streams are sent to chip 190 and processor 102. Step 504 executes by receiving the data streams at chip 190. Transceiver 182 may receive the information according to the Bluetooth™ standard. Step 506 executes by creating sets of data for the streams received at chip 190. A plurality of data points may be received from different sensors. This data should be correlated to appropriate sensor. Processor 102 may execute module 192 in doing this.

Step 508 executes by buffering the data sets generated by processor 102. The data set generation function is faster than the processing for determining deviation so the data sets should be buffered to prevent problems within chip 190. The data from the sensors may be buffered in memory 103. Clock counter 184 may place a time stamp or other indication on the buffered data while timer 186 executes a delay function before retrieving the data for processing. Alternatively, module 192 executed on processor 102 may act as a multiplexer and execute similar functions as multiplexer 114, but without hardware on chip 190. Memory 188 may store the data sets in a format that makes the information therein readily available to processor 102.

Step 510 executes by determining a difference in the data sets received by the sensors. In other words, any deviation from one data point to another may be tracked. For example, a slight change in position of colored pixels from the data provided by the sensors may be determined. The difference between data points may be used to determine whether a twitch by one of the eyes occurs or is about to occur. It also may be used to determine early movement of one of the eyes. Thus, step 512 executes by determining whether a twitch or early movement of one of the eyes is occurring. Step 512 may track the data received at chip 190 and determine the twitch or movement as opposed to a deviation of the eyes.

Step 514 executes by using a difference between the processed data from the sensors to determine the speed of deviation if one of the eyes is deviated. This information may be determined in conjunction with one that an eye is deviated, as disclosed above.

Figure 6:
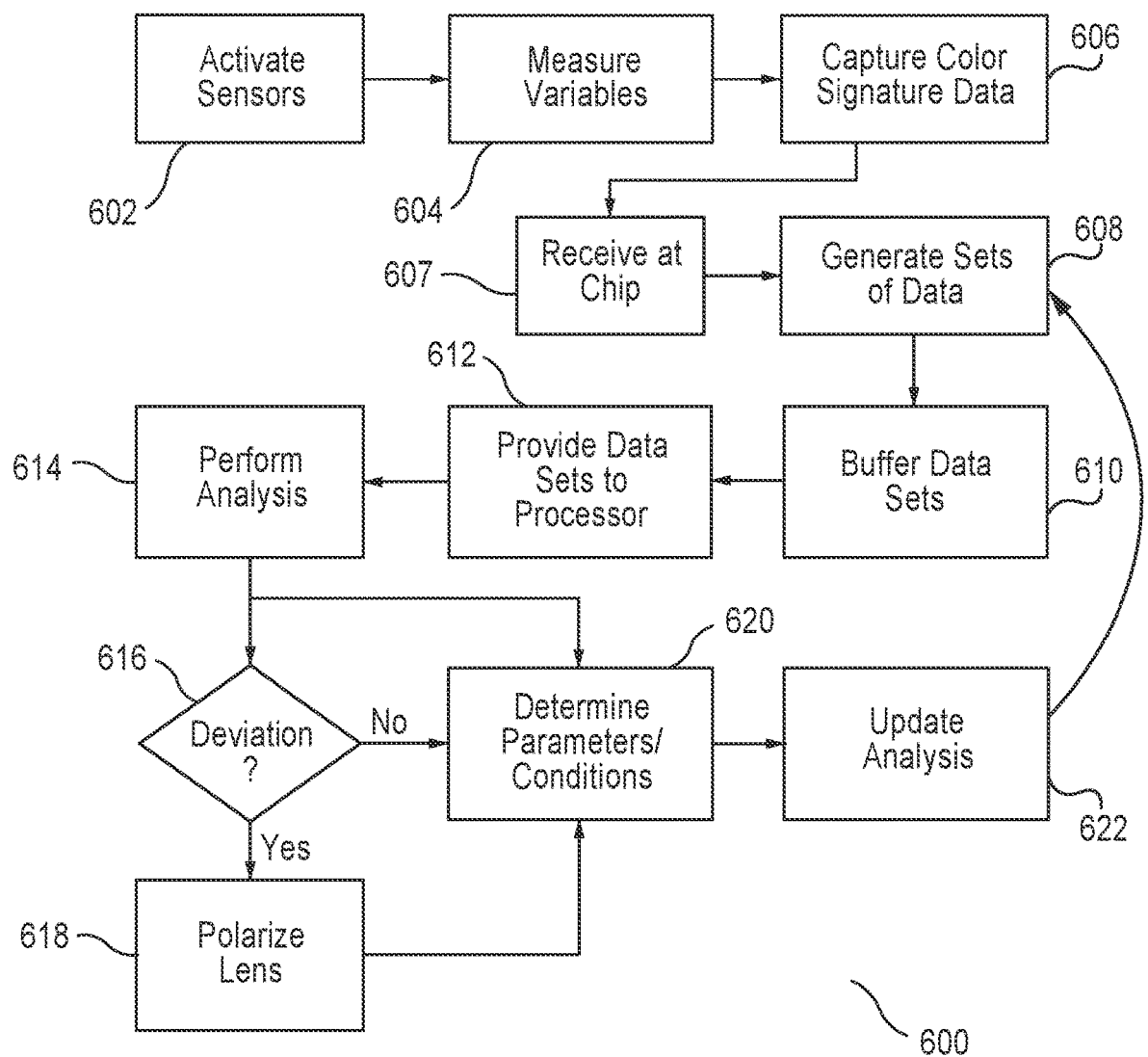
FIG. 6 illustrates a flowchart for processing data from sensors to determine deviation of an eye according to the disclosed embodiments.

FIG. 6 depicts a flowchart 600 for processing data from sensors to determine deviation of an eye according to the disclosed embodiments. Flowchart 600 may apply when large sets of data are captured by sensors 110 and 112 and analyzed for parameters or conditions with regards to the status of eyes 104 and 106. In addition to determining deviation of an eye, the disclosed embodiments may determine other parameters that can provide feedback to the system.

Step 602 executes by activating sensors 110 and 112. In some embodiments, sensors 110 and 112 are on glasses 116, as disclosed above. In other embodiments, the sensors are separate from the glasses and part of a device placed on the glasses to provide the functionality disclosed above. A signal may be received at the sensors to activate at specified times. Referring to FIG. 1C, timer 186 may activate the sensors periodically. In some embodiments, sensor 110 may actually be four sensors and sensor 112 also may be four sensors, each group located across an eye. Other numbers of sensors may be used.

Step 604 executes by measuring variables by the groups of sensors. The variables may relate to a current condition of each eye. For example, each sensor may measure four variables: red, green, blue, and luminosity. The data may relate to the detected levels of each variable based on the reflected light from an eye. The measured variables should provide a color signature of the eye. Step 606 executes by capturing the data generated by each sensor. For example, each sensor may measure the four variables at ten (10) times per second for a period of time, such as ten seconds. Timer 186 may implement the period for capturing the measured data. How fast or slow that data is captured and for how long may vary as desired. The sensors capture may capture raw data embodied by the variables, as opposed to an image.

Step 607 executes by receiving the captured data from each sensor at chip 190. The data should be organized by sensor and the measured variables. Step 608 executes by generating sets of data based on the measured variables in the captured data. For example, the data sets may comprise entries for the measured variables with corresponding captured values sorted by sensor. An example of a data set received from one group of four sensors may be shown in Table 1 below:

TABLE 1

| Data set counter, | Sensor #, | Red, | Green, | Blue, | Luminosity |
|---|---|---|---|---|---|
| 1 | 0 | Integer | Integer | Integer | Integer |
| 1 | 1 | Integer | Integer | Integer | Integer |
| 1 | 2 | Integer | Integer | Integer | Integer |
| 1 | 3 | Integer | Integer | Integer | Integer |
| 1 | 4 | Integer | Integer | Integer | Integer |
| 1 | 5 | Integer | Integer | Integer | Integer |
| 1 | 6 | Integer | Integer | Integer | Integer |
| 1 | 7 | Integer | Integer | Integer | Integer |
| 2 | 0 | Integer | Integer | Integer | Integer |
| 2 | 1 | Integer | Integer | Integer | Integer |
| 2 | 2 | Integer | Integer | Integer | Integer |
| 2 | 3 | Integer | Integer | Integer | Integer |
| 2 | 4 | Integer | Integer | Integer | Integer |
| 2 | 5 | Integer | Integer | Integer | Integer |
| 2 | 6 | Integer | Integer | Integer | Integer |
| 2 | 7 | Integer | Integer | Integer | Integer |

As can be appreciated, any number of sensors and measured variables may be used. Further, the data set would include much more entries as a set of 4 measured variables (in the columns) at 10 samples per second for 10 seconds using 4 sensors would yield 400 data points. Other formats for the data sets may be used. The features is capturing the measured variables over a period of time from a plurality of sensors to provide color signature information of the eye or eyes.

Step 610 executes by buffering the data sets. This step may be an optional step to make sure that the processor is not provided with data sets that it cannot process due to other functions being performed on chip 190. The processing for later analysis of the data sets may take longer than the data sets are formed. Thus, chip 190 may buffer the data sets in a memory, such as a cache memory or a queue. Alternatively, the data sets may be stored in one of the memory locations on chip 190. Each session may make use of clock counter 184 to stamp every reading or capture of data. For example, the data set may be output with session number/time stamp, red, blue, green, and luminosity. This example may be shown above in Table 1. As the collection sample is increased and decreased, the need for buffering may be more or less an issue. Faster processors may reduce or eliminate the need for buffering.

When instructed, step 612 executes by providing the data sets to the processor. Processor 102 may retrieve the data sets from the buffer memory. Step 614 executes by performing analysis using the information provided in the data sets. Processor 102 may analyze a wide range of information on all the measured variables within the data sets. For example, averages, peaks, moving averages, median values, deviations, and the like may be determined using the information to determine how the eye is acting. The average of the measured blue values of the four sensors of sensors 110 for eye 104 may be determined. The averages of all colors on the sensors of sensors 112 may be determined. Using this information, a deviation may be detected.

Step 616 executes by determining with a deviation of the eye or eyes has occurred based on the incoming data. Preferably, the disclosed embodiments analyzes the received measured variables to determine whether they have changed more than a set threshold for the color signature. In the disclosure provided above, the threshold may be 75%. If the measured values indicate a change in the color signature more than 75%, then the eyes are probably deviated. This threshold may be modified as needed so that it is more or less than 75%.

If step 616 is yes, then step 618 executes by polarizing the appropriate lens. System 100 may take an "ON" action to correct the deviated eye. In some embodiments, then may include polarizing optical glasses that are connected to chip 190 and sensors 110 and 112. Referring to glasses 116, they may polarize the appropriate lens, as disclosed above. Preferably, the lens on the non-deviated side of the pair of eyes is polarized. For example, referring back to FIG. 1A, if deviation is detected in eye 104 by sensors 110, then lens 120 is polarized as it corresponds to the non-deviated eye, or eye 106.

If step 616 is no, then step 620 may be executed by determining parameters or conditions based on the analysis of the data sets. Flowchart 600 also may arrive at step 620 directly from step 614 such that it occurs prior to or in conjunction with the deviation determination action in step 616. It also may proceed to step 620 from step 618 once corrective action is taking place so that one can review the parameters or conditions based on the information in the data sets. As disclosed above, parameters may include the speed of deviation of the eye, rate of change of the measured variables, differences between the variable measure angles, and the like. Conditions may include whether the changes are transient, such as a twitch, or whether the eye stays deviated after a sudden change. Other conditions may include movement of the eye in the course of normal activity.

Step 622 executes by updating the analysis process to have the disclosed embodiments learn over time the best way to determine deviations and conditions. The spread of the deviation may be a measure of the difference between all or some of the variables and how fast the readings are changing as well as how much they are changing may be used to improve the analysis of the subsequent data sets. The disclosed embodiments may recognize patterns of the color signature data as it is received to detect even faster than a deviation of the eye or eyes has occurred. Step 614 may be updated to include this information as part of the analysis as opposed to continuous processing of data sets. Flowchart 600 proceeds back to step 608 as well to continue monitoring the eyes and detecting any deviation.

The disclosed embodiments shown in FIGS. 2, 4, 5, and 6 include variables and values that may change depending on system 100 or glasses 116. Sample time for calibration, how fast data is collected, how the data is analyzed, what data is analyzed, the number of variables measured, and frequency of the measurements may all vary.

It will be apparent to those skilled in the art that various modifications to the disclosed may be made without departing from the spirit or scope of the invention. Thus, it is intended that the present invention covers the modifications and variations disclosed above provided that these changes come within the scope of the claims and their equivalents.

Without further elaboration, it is believed that one skilled in the art can, using the preceding description, utilize the present invention to its fullest extent. The preceding preferred specific embodiments are, therefore, to be construed as merely illustrative, and not limitative of the remainder of the disclosure in any way whatsoever.

In the foregoing and in the examples, all temperatures are set forth uncorrected in degrees Celsius and, all parts and percentages are by weight, unless otherwise indicated.

The entire disclosures of all applications, patents and publications, cited herein and of corresponding U.S. Provisional Application Ser. No. 62/294,135, filed Feb. 11, 2016, and U.S. patent application Ser. No. 15/431,207, filed Feb. 13, 2017, are incorporated by reference herein.

The preceding examples can be repeated with similar success by substituting the generically or specifically described reactants and/or operating conditions of this invention for those used in the preceding examples.

From the foregoing description, one skilled in the art can easily ascertain the essential characteristics of this invention and, without departing from the spirit and scope thereof, can make various changes and modifications of the invention to adapt it to various usages and conditions.

The invention claimed is:

1. A method for detecting a condition of an eye, the method comprising:
   capturing color signatures for an eye, wherein the color signatures include a color composition and a luminosity of light reflected from the eye;
   generating a plurality of data sets for the color signatures, wherein each data set includes measured values for the color composition and the luminosity;
   determining a deviation within the measured values between the plurality of data sets; and
   making opaque a lens to align the eye.

2. The method of claim 1, further comprising buffering the plurality of data sets after the generating step.

3. The method of claim 1, wherein the determining the deviation includes determining differences between the measured values between the plurality of data sets.

4. The method of claim 3, further comprising comparing the differences to a threshold to determine the deviation exists.

5. The method of claim 1, further comprising determining a parameter for the eye based on the measured values within the plurality of data sets.

6. The method of claim 1, wherein the measured values for the color composition of the color signatures includes measured values for red, blue, and green levels in the reflected light.

7. The method of claim 1, further comprising assigning a session value to each data set of the plurality of data sets.

8. The method of claim 1, further comprising providing the color signatures from a plurality of sensors to capture the reflected light.

9. The method of claim 1, wherein the making opaque step includes polarizing the lens.

10. A device to detect a condition of an eye, the device comprising:
    a processor to receive data from a plurality of sensors to receive reflected light from an eye, the processor configured to
    capture color signatures for the eye using the plurality of sensors, wherein the color signatures include a color composition and a luminosity of the reflected light;
    generate a plurality of data sets for the color signatures, wherein each data set includes measured values for the color composition and the luminosity;
    determine a deviation within the measured values between the plurality of data sets; and
    make opaque a lens to align the eye.

11. The device of claim 10, wherein the device includes glasses having the lens.

12. The device of claim 10, wherein the plurality of sensors include red-green-blue (RGB) sensors.

13. The device of claim 10, further comprising a multiplexer to receive the data from the plurality of sensors.

* * * * *